United States Patent [19]
Wishinsky

[11] Patent Number: 5,217,476
[45] Date of Patent: Jun. 8, 1993

[54] SURGICAL KNIFE BLADE AND METHOD OF PERFORMING CATARACT SURGERY UTILIZING A SURGICAL KNIFE BLADE

[75] Inventor: David H. Wishinsky, Rincon, P.R.

[73] Assignee: Medical Sterile Products, Inc., Rincon, P.R.

[21] Appl. No.: 769,389

[22] Filed: Oct. 1, 1991

[51] Int. Cl.$^5$ .............................................. A61B 17/32
[52] U.S. Cl. ................................... 606/167; 606/107; 128/751; 128/898
[58] Field of Search .............. 606/166, 167, 172, 185, 606/160, 4, 5, 6, 79, 161, 170, 173, 181; 30/41.8, 34.05, 123, 289, 368, 346.52; 128/751, 207.29, 754; 33/628; 7/158, 163, 170; 604/22

[56] References Cited

U.S. PATENT DOCUMENTS

| | | | |
|---|---|---|---|
| 140,336 | 7/1873 | Alexander | 7/163 |
| 354,800 | 12/1886 | McDonald | 7/163 |
| 4,337,773 | 7/1982 | Raftopoulos et al. | 128/754 |
| 4,340,059 | 7/1982 | Marinoff | 606/166 |
| 4,884,569 | 12/1989 | Fedorov et al. | 606/166 |
| 5,012,818 | 5/1991 | Joishy | 128/754 |
| 5,098,438 | 3/1992 | Siepser | 606/166 |

FOREIGN PATENT DOCUMENTS 759941 10/1956 United Kingdom ................. 111/99

Primary Examiner—Edgar S. Burr
Assistant Examiner—Ren Yan

[57] ABSTRACT

A surgical knife blade for forming an incision of predetermined length in bodily tissue includes indicia disposed adjacent opposing portions of a cutting edge such that alignment of the opposing indicia with the tissue during insertion of the knife blade in the tissue produces an incision of the predetermined length. A method of performing cataract surgery utilizes the surgical knife blade to precisely form a smaller incision for lens removal and a larger incision for implant of the intraocular lens.

15 Claims, 1 Drawing Sheet

SURGICAL KNIFE BLADE AND METHOD OF PERFORMING CATARACT SURGERY UTILIZING A SURGICAL KNIFE BLADE

BACKGROUND OF THE INVENTION

1. Field of the Invention

The present invention pertains to surgical knife blades and, more particularly, to a surgical knife blade for precisely forming incisions of predetermined lengths (sometimes referred to as incision widths) in bodily tissue and to a method of performing cataract surgery utilizing the surgical knife blade.

2. Discussion of the Prior Art

Many surgical procedures require the use of surgical knives for forming incisions in bodily tissue to provide access to a body cavity or internal operative site. Most surgical knives include a handle having a cutting blade mounted on a distal end thereof for being inserted in tissue to produce an incision. The cutting blades on surgical knives are usually of minimal thickness to penetrate tissue easily with minimal trauma such that the incisions can be closed without excessive stretching of surrounding tissue while promoting rapid healing with minimal scarring. The cutting blades on surgical knives are typically available in a variety of sizes and have a maximum width between opposing lateral sides of the blade, the blades being tapered to extend longitudinally in a distal direction from the area of maximum width to a sharp tip, or point, facilitating insertion of the blade in tissue. Accordingly, the lateral sides of the blades are configured to extend distally with a desired taper, and the exact configuration for the taper varies dependent upon the type of incision to be produced for a specific operative procedure or the desires of individual surgeons. When forming relatively long incisions, a blade is inserted in the bodily tissue in the manner of a plunge cut; and, once the tip or point has penetrated the tissue to the required depth for the operative procedure being performed, the blade is moved through the tissue in line with the lateral sides until an incision is produced having a length sufficient to provide access for the operative procedure. The length of the incision can be several times greater than the width of the blade; and, frequently, deviance of actual incision length from an optimal incision length for the operative procedure is not medically significant. However, many operative procedures require that the lengths of incisions be precisely formed to avoid damage to surrounding tissue and organs as well as other adverse complications of surgery.

In cataract surgery and other microsurgical procedures, the lengths of incisions must be very small; and, when forming incisions that are small in length, a knife blade having a known size, or maximum width, as close as possible to the length of incision desired is usually inserted in tissue in a direction normal thereto in the manner of a plunge cut to form an incision in the tissue surface extending lengthwise between the lateral sides of the blade. In other words, an incision having an end-to-end length corresponding to the known width of the blade is formed in the tissue surface when the blade is inserted deep enough to penetrate the tissue surface to the known blade width. Because individual knife blades are conventionally sized to reflect a single, known blade width, an individual blade can precisely form only a single incision of a predetermined width. The lengths of incisions that can be precisely formed utilizing conventional surgical knife blades are limited due to the knife blades being manufactured in a limited number of sizes, or widths. Consequently, in many cases the actual lengths of incisions made with surgical knife blades must be subjectively estimated during incision formation to approximate the optimal incision length, and the actual length of an incision thusly formed is not known absent the use of extraneous measuring devices.

In cataract surgery, the length of an incision made in the sclera or adjacent tissue must be large enough to provide access for lens removal yet no larger than necessary to avoid distortion of the curvature of the eye, or astigmatism, when the incision is closed. In lens removal and replacement surgery of the eye, an incision is made in the eye to be only large enough in length to permit removal of the natural lens due to a blindness causing condition, such as cataract. The optimal length for the incision is very small, i.e. approximately 3 mm, and a surgical knife blade having a known size, close to 3 mm is selected for forming the incision or a thin blade is used with a lateral cutting movement. With a surgeon manipulating the blade via the handle thereon, the tip of the blade is utilized to initially penetrate the sclera, and the blade is inserted while calipers set to 3 mm are held adjacent the incision to compare actual incision length with the calibrated length. If the length of the incision is smaller than desired, the blade is manipulated and incision length measurements are repeated until the proper length incision has been obtained. Once the incision is determined to be accurately formed, the blade is removed, and a surgical instrument is introduced through the incision to remove the natural lens in accordance with a procedure selected for lens removal, such as phacoemulsification. After the natural lens has been removed, a lens implant selected to replace the natural lens is inserted through the incision; and, in most cases, the initial incision must be lengthened to accommodate the implant. Usually, the length of the initial incision must be enlarged to at least 4 mm and, more typically, to approximately 5 mm. A second blade with a known size, as close as possible to the minimum length incision required to accommodate the implant is inserted in the initial incision in a direction normal to the sclera or the incision is enlarged with a smaller blade. As with the initial incision, calipers set to the desired length for the final incision are employed to compare the enlarged incision length with the desired length. Once the desired incision length if formed, the implant is inserted through the incision into the eye. The need for multiple blades having known sizes closely matching desired incision lengths and for measuring instruments to ascertain actual incision length significantly complicates and protracts the surgical procedure while the use of a blade smaller than the desired incision leads to inaccurate incision lengths.

Surgical blades suitable for use in microsurgery are exemplified by U.S. Pat. No. 4,793,218 to Jordan et al. The blades are provided with markings at spaced intervals along a single, tapered lateral edge thereof for alignment with a tissue surface to indicate the depth of the blades in tissue and thusly prevent damage to internal organs from the blades being inserted too far when forming incisions. However, the actual length of an incision produced with the blade when any one of the markings is aligned with the tissue surface is unknown. Additionally, if the blade is inserted in a tissue surface in a direction other than normal thereto, incisions of varying lengths are produced for the associated blade depth depending upon the angle of insertion of the blade.

SUMMARY OF THE INVENTION

Accordingly, it is a primary object of the present invention to overcome the aforementioned disadvantages of prior art surgical knife blades and methods of cataract surgery.

Another object of the present invention is to provide a surgical knife blade for precisely forming incisions of predetermined lengths (or widths) in bodily tissue.

An additional object of the present invention is to dispose indicia on opposing portions of a cutting edge of a surgical knife blade such that alignment of the opposing indicia with tissue produces an incision of a predetermined length.

It is also an object of the present invention to provide indicia on opposing portions of a tapered end of a surgical knife blade to indicate the length of an incision formed in tissue with the tapered end.

A further object of the present invention is to provide alignment markings adjacent lateral sides of a tapered end of a surgical knife blade for alignment with a tissue surface to form an incision having a length corresponding to the width between the lateral sides at the alignment markings.

Yet another object of the present invention is to provide a method of cataract surgery wherein a tapered end of a surgical knife blade is utilized to precisely form an incision of predetermined length in an eye.

An additional object of the present invention is to provide a method of cataract surgery wherein a single surgical knife blade is utilized to precisely form multiple incisions of predetermined lengths in an eye while indicating the lengths of the incisions thusly formed.

Some of the advantages of the present invention are that incisions very small in length and width can be accurately produced in bodily tissue, the need for subjective determinations of incision length when forming incisions in bodily tissue is eliminated, extraneous devices for measuring incision length need not be employed, formation of incisions that are larger or smaller than medically optimal is prevented, known surgical techniques for forming incisions in bodily tissue can be utilized, and corneal deformation, or astigmatism, as a consequence of cataract surgery is avoided.

The present invention is generally characterized in a surgical knife blade for forming an incision of predetermined length in bodily tissue formed of a body having a cutting edge terminating at a distal tip and configured to form an incision when the knife blade is moved in a cutting direction normal to the tissue and indicia carried on the body adjacent opposing portions of the cutting edge in alignment such that the width between the indicia portions is transverse to the cutting direction of movement of the knife blade and is parallel to the length of the incision to be formed, the width between the opposing portions of the cutting edge at the indicia corresponding to the predetermined length of the incision to be formed such that alignment of the indicia with the tissue creates the predetermined length incision. The present invention is also generally characterized in a method of performing cataract surgery utilizing a surgical knife blade as described above wherein the knife blade is inserted in the sclera or adjacent tissue until the indicia is aligned with the sclera to form an incision of a predetermined length, the knife blade is removed and the natural lens is removed from the eye through the incision.

Other objects and advantages of the present invention will become apparent from the following description of the preferred embodiment taken in conjunction with the accompanying drawings wherein like parts in each of the several figures are identified by the same reference characters.

DESCRIPTION OF THE PREFERRED EMBODIMENTS

Figure 1:
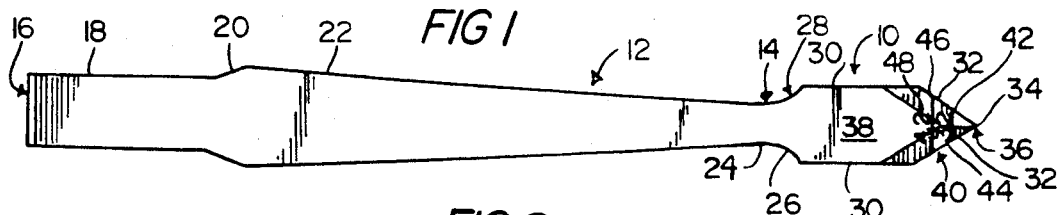
FIG. 1 is a plan view of a surgical knife blade according to the present invention.

A surgical knife blade 10 according to the present invention is shown in FIG. 1 attached to an elongated knife handle 12 having a distal end 14 coupled with the blade 10 and a proximal end 16. The handle 12 includes a base 18 of generally uniform width and thickness extending from the proximal end 16 to laterally, outwardly tapering shoulders 20 and a shank 22 joined to the shoulders 20 and extending with an inward taper from the shoulders 20 to a neck at the distal end 14. The handle 12 can have any desirable configuration to be easily and comfortably grasped by a surgeon to manipulate the blade 10.

The knife blade 10 has curved edges 26 at a proximal end 28 joined to the neck 24 of the handle, side or lateral edges 30 joined to the curved edges 26 and extending in symmetrical, parallel relation with a longitudinal axis passing through the blade and handle, and a cutting edge including opposing forward or distal cutting edge segments 32 joined to the lateral edges 30 and extending distally to meet at a point or tip 34 at a distal end 36 of the blade disposed on the longitudinal, axis of the blade. The side edges 30 and cutting edge segments 32 are defined by intersecting front and rear surfaces 38 of the blade, and the thickness of the blade between the front and rear surfaces is preferably very small to facilitate penetration of tissue to form a narrow width incision. The maximum linear distance between the lateral edges 30 measured transverse, or perpendicular, to the longitudinal axis of the blade 10 defines a maximum known width for the blade while the cutting edge segments 32 define a relatively smaller, variable width, tapered end extending distally from the maximum width. The width of the blade at any point along the tapered end 40 corresponds to the linear distance between opposing portions of the cutting edge segments 32 measured transverse, or perpendicular, to the longitudinal axis of the blade.

Indicia in the form of an alignment line 42 is provided on the tapered end 40 proximally spaced from the point 34 and extends across the tapered end between the cutting edge segments 32 in a direction transverse, or perpendicular, to the longitudinal axis of the blade. First and second indicia portions including opposing ends of the line 42 are disposed, respectively, adjacent the opposing portions of the cutting edge segments 32. Indicia 44 is disposed on the tapered end 40 adjacent the line 42 to indicate the width of the blade between the cutting edge segments 32 at the indicia portions transverse to the longitudinal axis of the blade along the line 42 or, in other words, to indicate the length of line 42. A second alignment line 46 extends across the tapered end 40 between the cutting edge segments 32 proximally spaced from and parallel with line 42, and third and fourth indicia portions including opposing ends of the line 46 are disposed, respectively, adjacent second opposing portions of cutting edge segments 32. Indicia 48 is disposed on the tapered end 40 adjacent the line 46 to indicate the width of the blade between the cutting edge segments 32 at the third and fourth indicia portions transverse to the longitudinal axis of the blade along the line 46 and, thus, the length of line 46, such length being greater than the length of line 42.

Preferably, the handle 12 and the blade 10 are made from a material suitable to be inserted in the body, such as stainless steel and the like. The blade 10 can be fabricated by forming blanks having the desired configuration from stainless steel by any suitable method including mechanical punching, cutting, electrical burning and photo-chemical machining. The cutting edge can be formed on blade 10 by grinding or otherwise sharpening the cutting edge segments 32 and the edges 30. The handle 12 can be made by forming blanks having the desired configuration from stainless steel; and, thereafter, the blade 10 can be attached to the handle by brazing, welding and the like. Alternatively, the handle 12 and the blade 10 can be unitarily, integrally formed from a single blank. According to a specific embodiment of the blade 10, the width of the blade at line 42 is 3.2 mm, the width of the blade at line 46 is 4.2 mm and the maximum width of the blade is 5.2 mm.

In use, the handle 12 is grasped by a surgeon to position the blade 10 normal to a surface of tissue to be penetrated, and the blade 10 is moved toward the tissue surface in a direction normal thereto with the longitudinal axis of the blade aligned with the direction of insertion to penetrate the tissue surface with the point 34. The blade 10 is inserted in the tissue with a plunge cut to align opposing ends of either of the alignment lines 42 or 46 with the tissue surface to precisely form an incision therein having a length (or width) from end-to-end corresponding to the width of the tapered end 40 at the selected alignment line. The indicia 44 and 48 identify the actual length of the incision thusly formed allowing actual incision length to be precisely controlled without the need for measuring devices. The blade 10 can be employed to precisely form multiple incisions of diverse lengths corresponding to the widths of the tapered end 40 at alignment lines 42 and 46 as well as the maximum known width of the blade between the lateral edges 30.

Figure 2:
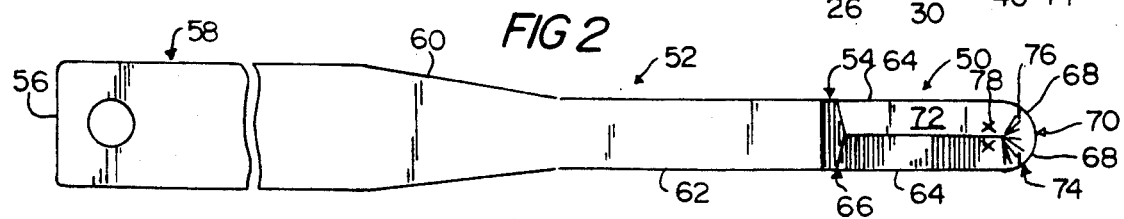
FIG. 2 is a plan view of another embodiment of a surgical knife blade according to the present invention.
Figure 3:
FIG. 3 is a side view of the surgical knife blade of FIG. 2.

Other embodiments of knife blades in accordance with the present invention are shown in FIGS. 2-6. A knife blade 50 is shown in FIGS. 2 and 3 attached to an elongated knife handle 52 having a distal end 54 coupled with the blade 50, a proximal end 56 and a longitudinal axis. The handle 52 includes a base 58 of generally uniform width and thickness extending lengthwise from the proximal end 56 to inwardly tapering shoulders 60 and a shank 62 of generally uniform width extending lengthwise from the shoulders 60 to the distal end 54. The blade 50 has lateral edges 64 joined to the shank 62 at a proximal end 66 of the blade and extending longitudinally therefrom in a distal direction in symmetrical, parallel relation with a longitudinal axis of the blade and a cutting edge including opposing arcuate distal cutting edge segments 68 joining the lateral edges 64 and extending distally from the lateral edges to meet at a distal end or tip 70 with the longitudinal axis of the blade being axially aligned with the handle longitudinal axis. The lateral edges 64 and the cutting edge segments 68 are defined by intersecting angled front and rear surfaces 72 on the blade, and the thickness of the blade between the front and rear surfaces 72 is minimal. The maximum linear distance between the lateral edges 64 measured transverse, or perpendicular, to the longitudinal axis of the blade 50 defines a maximum known width for the blade. The arcuate distal cutting edge segments 68 define a relatively smaller, variable width, tapered end 74 extending distally from the maximum width, and the width of the blade at any point along the tapered end 74 corresponds to the linear distance across the tapered end between opposing portions of the distal cutting edge segments 68 measured transverse to the longitudinal axis of the blade. The lateral edges 64 and the cutting edge segments 68 are sharpened continuously therealong to form a cutting edge for penetrating tissue.

A pair of opposed alignment lines or marks 76 are provided on the tapered end adjacent opposing portions of cutting edge segments 68, and the alignment marks 76 are laterally aligned perpendicular, or transverse, to the longitudinal axis of the blade 50 or, in other words, transverse to the direction of insertion of the blade. Indicia 78 on blade 50 adjacent alignment marks 76 indicates the width of the blade transverse to the longitudinal axis of the blade at marks 76.

Figure 4:
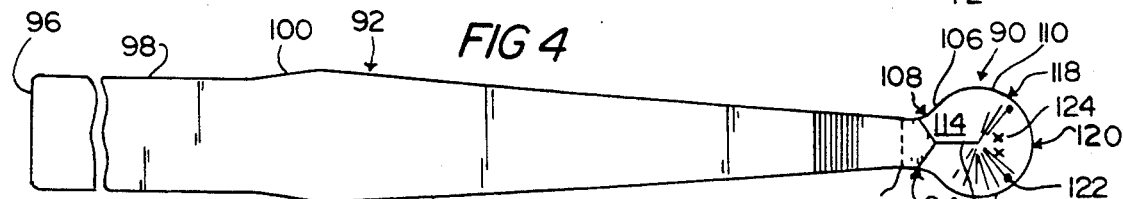
FIG. 4 is a plan view of a further embodiment of a surgical knife blade according to the present invention.
Figure 5:
FIG. 5 is a side view of the surgical knife blade of FIG. 4.

Another embodiment of a knife blade according to the present invention is shown in FIGS. 4 and 5. A knife blade 90 is attached to an elongated knife handle 92 having a distal end 94 coupled with the blade 90 and a proximal end 96. The handle 92 includes a base 98 of generally uniform width and thickness extending lengthwise from the proximal end 96 to laterally outwardly tapering shoulders 100, a shank 102 of generally uniform thickness extending lengthwise with an inward taper from the shoulders 100, a central longitudinal axis through base 98 and shank 102, and a neck 104 bent angularly from the shank 102 and extending to the distal end 94. The knife blade 90 includes proximal curved edges 106 joined at a proximal end 108 thereof to the neck 104 and extending outwardly therefrom and a cutting edge including continuously curving, opposing arcuate cutting edge segments 110 joining the proximal edges 106 and extending distally to meet at distal end or tip 120. The arcuate edge segments 110 are formed by a flat, rear surface 112 on the blade intersecting a front surface 114 on the blade tapering to a ridge 116 aligned with a diametric, longitudinal axis of the blade. The longitudinal axis of the blade 90 is contained in a plane containing the longitudinal axis of the base 98 and shank 102 and is angularly disposed with the longitudinal axis of the base and shank. The maximum diametric distance across blade 90 transverse, or perpendicular, to the longitudinal axis of the blade defines a maximum known width for the blade, and the arcuate edge segments 110 define a relatively smaller, variable width tapered end 118 extending distally of the maximum known width. The arcuate edge segments 110 are sharpened continuously therealong to form a cutting edge for penetrating tissue. A pair of alignment dots 122 are provided on tapered end 118 adjacent opposing portions of, respectively, the edge segments 110 in lateral alignment perpendicular, or transverse, to the axis of the blade 90, and indicia 124 is positioned on the blade adjacent the dots 122 to indicate the width of the blade at the dots 122 transverse to the central longitudinal axis of the blades.

Figure 6:
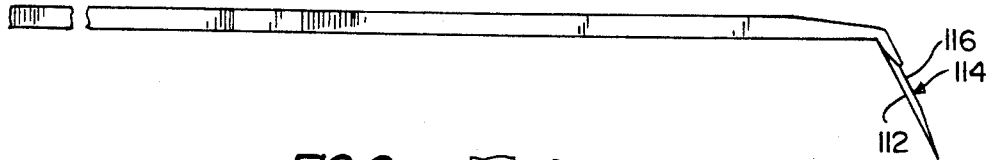
FIG. 6 is a broken plan view of another embodiment of a surgical knife blade according to the present invention.

Another embodiment of a knife blade according to the present invention is shown in FIG. 6 wherein a knife blade 130 is shown attached to the neck 24 of the handle 12 of FIG. 1. The knife blade 130 includes curved edges 132 joined at a proximal end 134 thereof to the neck 24 of the handle, side or lateral edges 136 joined to the curved edges 132 and extending lengthwise therefrom in the distal direction in symmetrical, parallel relation with a longitudinal axis of the blade and a cutting edge including a cutting edge segment 147 disposed along a longer one of the side edges 136 and an opposing forward cutting edge segment 138 angularly joining the longer side edge to a shorter one of the side edges 136 with the cutting edge segments 147 and 138 meeting at tip 142. The maximum linear distance between the lateral edges 136 measured transverse, or perpendicular, to the longitudinal axis of the blade defines a maximum known width for the blade, and the forward edge 138 and the longer lateral edge 136 define a relatively smaller, variable width tapered end 140 extending distally from the maximum width to a point 142 at a distal end 144 of the blade. The width of the blade at any point along the end 140 corresponds to the linear distance between opposing portions of the forward edge segment 138 and the longer lateral edge 136 transverse to the longitudinal axis of the blade. The forward edge segment 138 is sharpened continuously therealong to form a cutting edge for penetrating tissue. An alignment line 146 is provided on the end 140 proximally spaced from the point 142 and extends across the tapered end between the forward edge segment 138 and the longer lateral edge 136 transverse, or perpendicular, to the longitudinal axis of the blade, with opposing ends of the line 146 disposed adjacent the opposing portions of forward edge segment and longer lateral edge, respectively. Indicia is provided adjacent the alignment line 146 to indicate the width of the blade at the line 146 or, in other words, the linear distance between the forward edge segment 138 and the longer lateral edge 136 at line 146 transverse to the longitudinal axis of the blade. According to a specific embodiment, the width of the blade at line 146 is 3 mm and the maximum width of the blade is 5 mm.

Figure 7:
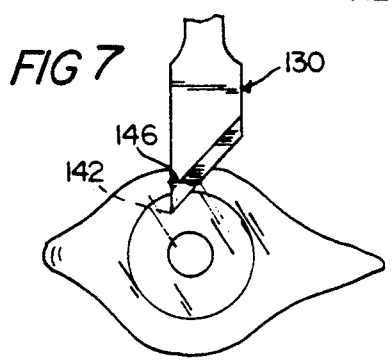
FIG. 7 is a broken plan view of the knife blade of FIG. 6 forming an incision in an eye.
Figure 8:
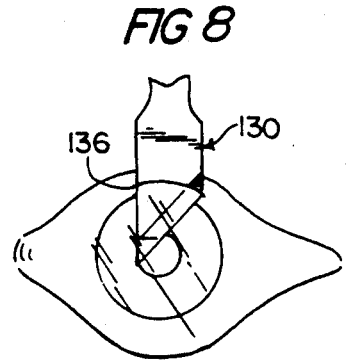
FIG. 8 is a broken plan view of the knife blade of FIG. 6 forming a second, relatively greater length incision in an eye.

FIGS. 7 and 8 show blade 130 being utilized in cataract surgery on the eye. After opening the conjunctiva, the sclera is penetrated with the point 142 which is laterally offset from the longitudinal axis of the knife blade; and, with the blade positioned normal to the outer surface, the tapered end 140 is inserted through the sclera in a direction normal thereto with the longitudinal axis of the blade aligned with the direction of insertion. By inserting the knife blade to a depth where the opposing ends of the alignment line 146 are aligned with the sclera, an incision having a precise length of 3 mm is produced as visually indicated by the indicia 148. The blade 130 is then removed from the eye, and instruments are inserted into the eye via the incision for removal of the natural lens, such as a phacoemulsification probe. Once the natural lens has been removed, the blade 130 is reinserted through the initial incision, with the longitudinal axis of the blade aligned with the direction of insertion, to a depth to position the lateral edges 136 in the sclera such that the maximum blade width is aligned with or disposed in the sclera to form an incision therein that is precisely 5 m in length. The blade 130 is then removed from the eye to permit an intraocular lens implant to be inserted in the eye through the newly formed, enlarged incision.

From the above it will be appreciated that incisions can be formed in the tissue of a precise predetermined length with the surgical knife blade of the present invention in an efficacious manner by simply inserting the blade into the tissue in a direction perpendicular to the tissue until indicia on opposing portions of the cutting edge of the knife blade are aligned with the tissue thereby defining the incision length. For cataract surgery, the surgical knife blade of the present invention is particularly advantageous due to the requirement that incisions are accurately formed to minimize incision length dependent upon the step of the procedure to be formed such as a small incision for lens removal via phacoemulsification and a larger incision for implant of an intraocular lens.

Inasmuch as the present invention is subject to many variations, modifications and changes in detail, the subject matter discussed above and shown in the accompanying drawings is intended to be illustrative only and not to be taken in a limiting sense.

What is claimed is:

1. A surgical knife blade for forming an incision of predetermined length in bodily tissue comprising
   a body having a cutting edge terminating at a distal tip, said cutting edge including opposing cutting edge segments extending distally to meet at said tip, said cutting edge being configured to form an incision in the tissue when said body is moved in a cutting direction transverse to the tissue to cause said tip to enter the tissue, the incision having a length transverse to the cutting direction of movement of said body; and
   indicia carried on said body including first and second portions disposed, respectively, adjacent opposing portions of said cutting edge segments in alignment such that the width of said body between said cutting edge segments at said first and second indicia portions is transverse to the cutting direction of movement of said body and is parallel to the length of the incision, said width corresponding to said predetermined length of the incision whereby alignment of said first and second indicia portions with said tissue creates said predetermined length incision.

2. A surgical knife blade as recited in claim 1 wherein said indicia visually identifies said predetermined length.

3. A surgical knife blade as recited in claim 1 wherein said body has a longitudinal axis aligned with said distal tip and said cutting edge includes opposing, tapering lateral edges.

4. A surgical knife blade as recited in claim 1 wherein said body includes a longitudinal axis, said distal tip is laterally offset from said longitudinal axis, and said cutting edge segments include an edge parallel with said longitudinal axis and an edge angularly joined to said parallel edge at said distal tip.

5. A surgical knife blade as recited in claim 1 wherein said indicia includes a line extending between said opposing cutting edge portions transverse to the cutting direction of movement.

6. A surgical knife blade as recited in claim 1 further comprising second indicia carried on said body including third and fourth portions disposed, respectively, adjacent second opposing portions of said cutting edge segments in alignment such that the width of said body between said cutting edge segments at said third and fourth indicia portions is transverse to the cutting direction of movement of said body and is parallel to the length of the incision, said width corresponding to a second predetermined length of the incision greater than said first mentioned predetermined length.

7. A surgical knife blade as recited in claim 6 wherein said second indicia visually identifies said second predetermined length.

8. A surgical knife blade as recited in claim 1 wherein said cutting edge segments have an arcuate configuration.

9. A surgical knife blade for forming an incision of predetermined length in bodily tissue comprising
body means having a proximal end, a longitudinal axis and a tapered distal end for insertion in the tissue in a direction aligned with said axis;
opposing edge means on said body means extending longitudinally to said distal end and spaced laterally in a direction transverse to said axis for forming an incision in the tissue, said body means having a blade width defined between said edge means transverse to said direction of insertion, said blade width being variable along said tapered end;
a predetermined blade width defined between said edge means along said tapered end transverse to said direction of insertion, said predetermined blade width being equal to said predetermined length of incision; and
means on said tapered end disposed, respectively, along said opposing edge means for being aligned with the tissue when said tapered end is inserted in the tissue in said direction of insertion whereby said predetermined blade width is aligned with the tissue to form an incision of said predetermined length.

10. A surgical knife blade as recited in claim 9 wherein a maximum blade width is defined between said edge means, said tapered distal end extends longitudinally from said maximum blade width in a distal direction, and said blade width along said tapered end is less than said maximum blade width.

11. A surgical knife blade as recited in claim 10 wherein said alignment means includes alignment marks disposed, respectively, adjacent said opposing edge means on said tapered end at said predetermined width.

12. A surgical knife blade as recited in claim 11 further including indicia on said body means identifying said predetermined width.

13. A method of performing cataract surgery comprising the steps of
providing a surgical knife blade having a longitudinal axis, a distal end for penetrating tissue, said distal end having opposing portions aligned in a direction transverse to said axis and a width defined between said opposing portions in the transverse direction, and indicia disposed, respectively, on said opposing portions;
inserting the distal end of the knife blade in the sclera or adjacent tissue in a direction aligned with the longitudinal axis until the indicia are aligned with the tissue to form an incision of a predetermined length corresponding to said width;
removing the knife blade from the eye; and
removing the natural lens from the eye through the incision.

14. A method of performing cataract surgery as recited in claim 13 further including the steps of
providing the surgical knife blade with second indicia disposed, respectively, on second opposing portions of the distal end, said distal end having a second width between said second opposing portions greater than the width between the first mentioned opposing portions;
reinserting the knife blade in the tissue through the incision in a direction aligned with the longitudinal axis until the second indicia are aligned with the tissue to enlarge the incision to a second predetermined length corresponding to said second width; and
inserting an intraocular lens through the enlarged incision.

15. A method of performing cataract surgery as recited in claim 14 wherein the predetermined length is approximately 3 mm and the second enlarged predetermined length is approximately 5 mm.

* * * * *